· US010966852B2

(12) United States Patent
Tsunoda

(10) Patent No.: US 10,966,852 B2
(45) Date of Patent: Apr. 6, 2021

(54) HEEL ANKLE SUPPORTER

(71) Applicant: Noriomi Tsunoda, Tokyo (JP)

(72) Inventor: Noriomi Tsunoda, Tokyo (JP)

(*) Notice: Subject to any disclaimer, the term of this patent is extended or adjusted under 35 U.S.C. 154(b) by 0 days.

(21) Appl. No.: 16/301,410

(22) PCT Filed: Feb. 15, 2018

(86) PCT No.: PCT/JP2018/005253
§ 371 (c)(1),
(2) Date: Nov. 13, 2018

(87) PCT Pub. No.: WO2019/159281
PCT Pub. Date: Aug. 22, 2019

(65) Prior Publication Data
US 2020/0163789 A1 May 28, 2020

(51) Int. Cl.
*A61F 5/01* (2006.01)
*A41D 13/06* (2006.01)
*A63B 71/12* (2006.01)

(52) U.S. Cl.
CPC ............ *A61F 5/0111* (2013.01); *A41D 13/06* (2013.01); *A63B 71/12* (2013.01); *A63B 2071/1275* (2013.01)

(58) Field of Classification Search
CPC .... A61F 5/0111; A61F 5/0113; A61F 5/0127; A61F 5/01; A61F 5/0102; A61F 5/0104; A63B 2071/1275; A63B 2071/1283; A41D 13/06
USPC .......... 602/27–29, 63, 65; 128/882, 892–894
See application file for complete search history.

(56) References Cited

U.S. PATENT DOCUMENTS

| 1,374,669 | A | * | 4/1921 | McClellan | ............ | A61F 13/066 |
| | | | | | | 602/62 |
| 4,729,370 | A | * | 3/1988 | Kallassy | ............... | A61F 13/066 |
| | | | | | | 602/65 |
| 4,844,058 | A | * | 7/1989 | Vogelbach | ............ | A61F 13/066 |
| | | | | | | 602/27 |
| 5,050,620 | A | * | 9/1991 | Cooper | ................. | A61F 13/066 |
| | | | | | | 602/27 |

(Continued)

FOREIGN PATENT DOCUMENTS

| JP | H10-248865 A | 9/1998 |
| JP | 2006-158833 A | 6/2006 |

(Continued)

OTHER PUBLICATIONS

International Search Report and Written Opinion of related International Patent Application No. PCT/JP2018/005253 dated Mar. 20, 2018.

*Primary Examiner* — Kari K Rodriquez
(74) *Attorney, Agent, or Firm* — Arent Fox LLP

(57) ABSTRACT

Provided with a sleeve supporter which can cover a surface of an region including an instep, a sole, a heel and an ankle of a foot and a belt-type supporter which is attached to the sleeve supporter and attachable to the foot on the sleeve supporter: the belt-type supporter is provided with an ankle belt, a plantar heel hold belt, an affected-part pressing belt and a posterior heel hold belt: the sleeve supporter is made of cloth having an extension larger than that of the belt-type supporter, yarns used therefor have a thickness 30 denier to 70 denier (both inclusive) and a clothing pressure thereof is 10 mmHg to 20 mmHg (both inclusive).

7 Claims, 19 Drawing Sheets

(56) References Cited

U.S. PATENT DOCUMENTS

| | | | | |
|---|---|---|---|---|
| 5,067,486 A * | 11/1991 | Hely | ............... | A61F 13/066 |
| | | | | 602/27 |
| 5,099,860 A * | 3/1992 | Amrein | ............ | A61F 5/0111 |
| | | | | 128/882 |
| 5,217,431 A * | 6/1993 | Toronto | ............ | A61F 5/0111 |
| | | | | 602/27 |
| 5,620,413 A * | 4/1997 | Olson | ............ | A61F 5/0111 |
| | | | | 602/27 |
| 7,115,105 B2 * | 10/2006 | Cropper | ............ | A61F 5/0111 |
| | | | | 602/27 |
| 7,267,656 B2 * | 9/2007 | Cooper | ............ | A61F 5/0111 |
| | | | | 602/27 |
| 2004/0260226 A1 * | 12/2004 | Gilmour | ............ | A61F 13/066 |
| | | | | 602/65 |
| 2006/0211968 A1 * | 9/2006 | Gordon, Jr. | ......... | A61F 5/0111 |
| | | | | 602/27 |
| 2007/0049856 A1 * | 3/2007 | Arensdorf | ......... | A61F 5/0111 |
| | | | | 602/27 |
| 2007/0149908 A1 * | 6/2007 | Gordon, Jr. | ......... | A61F 5/0111 |
| | | | | 602/27 |
| 2011/0092867 A1 * | 4/2011 | Watts | ............ | A61F 5/0111 |
| | | | | 602/27 |

FOREIGN PATENT DOCUMENTS

| | | | |
|---|---|---|---|
| JP | 3990494 | B2 | 10/2007 |
| JP | 2010-131067 | A | 6/2010 |
| JP | 2012-249864 | A | 12/2012 |
| JP | 3191369 | U | 6/2014 |
| JP | 2016-214649 | A | 12/2016 |
| JP | 6142350 | B1 | 6/2017 |
| JP | 2017-192570 | A | 10/2017 |

\* cited by examiner

HEEL ANKLE SUPPORTER

CROSS-REFERENCE TO RELATED APPLICATIONS

This application is a National Stage Entry of International Patent Application PCT/JP2018/005253, filed Feb. 15, 2018. The disclosure of the priority application incorporated in their entirety herein by reference.

BACKGROUND OF THE INVENTION

Technical Field

The present invention relates to a heel ankle supporter which enables to correct bones and joints around an ankle by suitably supporting the bones, joints and muscles around the ankle.

Background Art

Conventionally, various supporters are used for purposes of heat retention and of preventing sprains owing to ankle varus.

For example, Patent Document 1 proposes a foot joint taping supporter having an anchor strap, a figure-8 strap, and a stirrup strap. The anchor strap is tightly wound around an ankle. The figure-8 strap is tightly wound in a figure-8 so as to pass along an instep and a sole of a foot, starting from its outside, and pass along the instep again, and reach a posterior side of the foot. The anchor strap and the figure-8 strap are formed integrally from an elastic tape having a hook-and-loop fastener on its outer surface. The stirrup strap is fixed at one end to the anchor strap and tightly wound passing along the sole of the foot from a medial malleolus to a lateral malleolus. Patent Document 1 describes that it is possible by the foot joint taping supporter to energize the ankle in a valgus direction so as to prevent varus and valgus of an ankle by tightly winding the stirrup strap from the inside passing along the sole of the foot so as not to restrain plantar flexion and dorsal flexion though the stirrup strap is hard to stretch in a longitudinal direction.

Patent Document 2 proposes a foot joint supporter having a foot joint cover body and a belt piece for fixing which are integrally provided into substantially a T-shape: in the foot joint cover body, a sleeve part is formed to expose a tip and a heel of the foot when it is equipped; and in the belt piece for fixing, both ends in a longitudinal direction is free in a front of a part corresponding to a sole of the foot of the sleeve part. Patent Document 2 describes that: a posterior side of the foot joint cover body can be open by opening overlapped fastening pieces; after inserting the foot from there into the sleeve part, by fastening the overlapped fastening pieces and fastening both the ends of the belt piece for fixing so as to pass through an instep toward malleoli while intersecting each other, the foot joint supporter can be easily equipped on a foot joint part: so that the foot joint part can be stabilized and held rigidly and exactly by the foot joint cover body and the belt piece for fixing.

Conventionally, regarding varus sprain at an ankle, acute symptoms and irregular pain in a chronic phase are treated by the above-mentioned ankle supporters. However, it is not possible for such supporters for the inversion sprain to support unstable symptoms in a wide range around the ankle such as protection, correction of an talus and a calcaneus bone, and a relief of a symptom of an injury, even though some symptoms can be ease. Accordingly, a supporter which can support these unstable symptoms in a wide range is required.

Therefore, the present applicant provides a heel ankle supporter including a heel-hold belt and a talus bone pressing belt in Patent Document 3. Moreover, the present applicant improves the heel ankle supporter disclosed in Patent Document 3 and provides a heel ankle supporter including an ankle belt, a plantar heel hold belt, an affected-part pressing belt and a posterior heel hold belt in Patent Document 4. It is possible to effectively protect bones, joints and injuries around an ankle by these heel ankle supporters.

CITATION LIST

Patent Literature

Patent Document 1: Japanese Unexamined Patent Application, First Publication No. H10-248865
Patent Document 2: Japanese Patent No. 3990494
Patent Document 3: Japanese Unexamined Patent Application, First Publication No. 2016-214649
Patent Document 4: Japanese Unexamined Patent Application, First Publication No. 2017-192570

SUMMARY OF INVENTION

Problem to be Solved by the Invention

The present invention has an object to further improve function of the heel ankle supporter and provide a heel ankle supporter which can effectively protect bones, joints and injury around an ankle, which enables to correct the bones and the joints and to buffer symptoms of the injury around the ankle; and which can protect muscles around the bones along with the bones, prevent excessive extension of the muscles, and prevent a pulled muscle and a ligament rupture while correcting.

Solution to Problem

The present invention is a heel ankle supporter having elasticity wearable for a foot of a human body, including a sleeve supporter which can cover a surface of a region including an instep, a sole, a heel and an ankle of the foot, and a belt-type supporter which is fixed to the sleeve supporter and wearable for the foot on the sleeve supporter: the belt-type supporter is provided with an ankle belt, a plantar heel hold belt, an affected-part pressing belt, and a posterior heel hold belt which are respectively formed into a belt shape: the ankle belt is fixable to the ankle by being wound around the ankle above a medial malleolus and a lateral malleolus of the foot; in the plantar heel hold belt, one end in a longitudinal direction is fixed to the ankle belt so as to extend downward from the ankle belt from the one end toward the other end, the plantar heel hold belt is provided with an inner cover part configured to continue from the ankle belt so as to cover a vicinity of the medial malleolus; a plantar cover part configured to continue from the inner cover part so as to cover the sole at a front of a calcaneus, and an outer cover part provided configured to continue from the plantar cover part so as to cover a vicinity of the lateral malleolus; the other end of the plantar heel hold belt is fixed to an outer surface of the ankle belt so that the plantar heel hold belt is fixable to the foot passing through the sole in an extended state, the affected-part pressing belt is fixed to the plantar heel hold belt at one end in a longitudinal direction, configured to extend diagonally forward in a direction gradually separated from the plantar heel hold belt from the one end to the other end, and provided with a pressing part which is wound in a direction from an outside of the foot to an inside of the foot through the instep side so as to cover an affected part, the other end of the affected-part pressing belt is fixed to any one of outer surfaces of the ankle belt, the plantar heel hold belt or the affected-part pressing belt in a middle position along a longitudinal direction so as to be fixed to the foot and cover the affected part in an extended state, the posterior heel hold belt is fixed to the plantar heel hold belt below the medial malleolus and the lateral malleolus at one end in a longitudinal direction, configured to extend backward from the plantar heel hold belt parallel to the ankle belt, provided with a posterior cover part so as to cover a posterior part of a vicinity of the calcaneus, and fixed to an outer surface of the outer cover part at the other end so as to be fixed to the heel of the foot covering the posterior part in an extended state, and the sleeve supporter is made of cloth and a thickness of yarn used for it is not smaller than 30 denier and not more than 70 denier, clothing pressure is not less than 10 mmHg but not more than 20 mmHg.

According to this heel ankle supporter, the sleeve supporter covers the region including the instep, the sole, the heel and the ankle, and the ankle belt fixed around the ankle and the plantar heel hold belt wound and fixed from the medial malleolus side to the lateral malleolus side passing through the sole in the front of the calcaneus are attached on the sleeve supporter, so that the heel ankle supporter can be fixed to the foot. Although sizes of a foot vary depending on persons, since the sleeve supporter has the elasticity and the ankle belt and the plantar heel hold belt are attached to the foot by winding respective belt-shaped belts, it is possible to finely adjust positions of the ankle belt and the plantar heel hold belt with a size of a foot individually. Accordingly, the heel ankle supporter can be stably worn suitably for an individual foot.

In the heel ankle supporter, the posterior heel hold belt is wound and fixed below the medial malleolus and the lateral malleolus from the inside to the outside of the foot passing through the posterior part in the vicinity of the calcaneus, so it is possible to prevent adduction of the calcaneus and rigidly correct the adducted calcaneus. Since the ankle belt and the plantar heel hold belt are stably fixed to the foot, the posterior heel hold belt is also stably fixed, so it is possible to reliably stabilize the calcaneus at a stable position by the posterior heel hold belt.

By the affected-part pressing belt provided at the heel-ankle belt, the affected part can be covered and further pressed with intention of protection and treatment of the affected part with various symptoms of injuries. In the heel ankle supporter, it is possible to finely adapt the position of the plantar heel hold belt to a position of the affected part, so that the affected-part pressing belt can be stably pressed on the affected part. Furthermore, with respect to the posterior heel hold belt extending backward from the plantar heel hold belt, the affected-part pressing belt is extended diagonally forward from the plantar heel hold belt; so that tension force added on the plantar heel hold belt between the affected-part pressing belt and the posterior heel hold belt can be balanced when the posterior heel hold belt is fixed to the heel. Therefore, it is possible to rigidly fix the posterior heel hold belt to the heel in a stable state.

As described above, the heel ankle supporter can be stably worn on an individual foot without differences among individuals, thereby stabilizing the calcaneus stably: accordingly, it is possible to protect and treat the affected part while reliably preventing and correcting right and left malposition (deviation) of the calcaneus. Furthermore, the affected parts are reliably pressed by the affected-part pressing belt so it is possible to protect the bones, the joints and the injuries around the ankle effectively: so it is possible to correct the bones and the joints around the ankle and assuage the symptoms of the injuries, and it is possible to perform treatments with high flexibility. Moreover, by the heel ankle supporter, it is possible to expect to prevent sprains by adjusting axes of the joints of the foot, improve an arch shape of the sole, prevent gonarthrosis, coxarthropathy and bow-legs and the like by normalizing the axes of the joints of the foot, and prevent lumbago by supporting a trunk of a body.

In this case, the sleeve supporter covers the surface of the region including the instep, the sole, the heel and the ankle and the belt-type supporter is wound thereon and fixed, so that the belt-type supporter is not directly in contact with skin and not easy to be slipped. Accordingly, it is possible to stably use without a rash and a skin abrasion by the slippage.

Since the sleeve supporter has a prescribed elasticity, it is possible to wrap and press the whole surface of the region including the instep, the sole, the heel and the ankle appropriately. Accordingly, it is possible to add a fastening force of the belt-type supporter attached on the sleeve supporter not only directly under the belt, but also on the region in the vicinity of the belt through the sleeve supporter; so that it is possible to broadly press not only the bones but muscles. Therefore, it is possible to prevent the muscles from excessive extension when a person wearing the heel ankle supporter is attached acts such as walking. The sleeve supporter is formed to have the thickness of yarn of 30 denier to 70 denier (both inclusive) and has the clothing pressure of 10 mmHg to 20 mmHg (both inclusive), so that the foot is not excessively pressed and appropriate exercises of the muscles are not prevented.

It is preferable that the sleeve supporter have larger extension than those of the belts of the belt-type supporter.

As a desirable embodiment of the heel ankle supporter according to the present invention, the belt-type supporter is detachable to the sleeve supporter and the sleeve supporter has belt loops in which the ankle belt is passed through and held. It is possible to fix the sleeve supporter and the belt-type supporter to the appropriate positions respectively. The ankle belt of the belt-type supporter is passed through the belt loops of the sleeve supporter, thereby enabling the sleeve supporter and the belt-type supporter to be treated as one, and it is possible to reliably prevent slippage in an attached state.

As another embodiment of the heel ankle supporter according to the present invention, the posterior heel hold belt may be detachable to the belt-type supporter. If it is not necessary to support the heel or support the Achilles' tendon, it is possible to use in a state in which the posterior heel hold belt is taken off, and use appropriately in accordance with a symptom of a patient.

As another embodiment of the heel ankle supporter according to the present invention, an instep hold belt may be configured to be detachable to a tip end of the sleeve supporter so as to stabilize a part including the instep and the sole by winding one or more rounds. If it is necessary to mend an injury at the instep or absorb a shock on the instep, it is possible to attach and use the instep hold belt.

As another embodiment of the heel ankle supporter according to the present invention, the posterior heel hold belt may be configured from two belts which are a first posterior heel hold belt and a second posterior heel hold belt: the first posterior heel hold belt is provided at a position near to the sole below the medial malleolus and the lateral malleolus; and the second posterior heel hold belt is provided at a position nearer to the medial malleolus and the lateral malleolus than that of the first posterior heel hold belt. Adjusting fixing forces of the first posterior heel hold belt and the second posterior heel hold belt, it is possible to stabilize the foot in an appropriate state in accordance with a symptom of a sprain and the like.

As another embodiment of the heel ankle supporter according to the present invention, the first posterior heel hold belt may be fixed to an inner cover part of the plantar heel hold belt at one end; and the second posterior heel hold belt may be fixed to an outer cover part of the plantar heel hold belt at one end. It is possible for the first posterior heel hold belt and the second posterior heel hold belt to add forces in counter directions with each other, so that the foot can be stabilized in a state more appropriately by adjusting these fixing forces.

As an embodiment of the heel ankle supporter of the present invention, it is preferable that the sleeve supporter be formed from moisture absorbing heat generation cloth. It is possible to solve coldness and swelling of a foot and a bad condition of an autonomic nerve and chromic ischemia owing to the coldness of the foot.

Advantageous Effects of Invention

According to the heel ankle supporter of the present invention, combining the ankle belt, the plantar heel hold belt, the affected-part pressing belt and the posterior heel hold belt which are formed to have a belt-shape; it is possible to protect the bones, the joints and the injuries around the ankle effectively, and it is possible to correct the bones and the joints and ease the injury symptoms, around the ankle. By the sleeve supporter, it is possible to protect the bones and also the muscles around the bones, prevent the excessive extension of the muscles, and prevent the pulled muscles, the ligament raptures and the like while correction.

DESCRIPTION OF EMBODIMENTS

Figure 1:
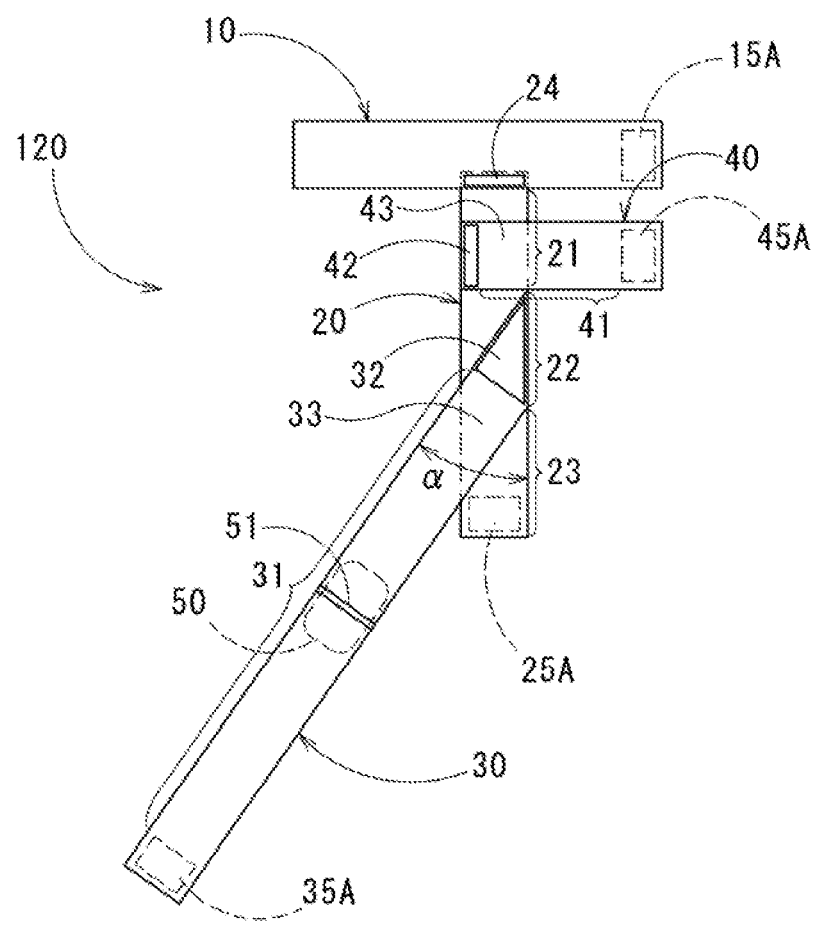
FIG. 1 It is a plan view showing an outer surface of a belt-type supporter in a heel ankle supporter according to a first embodiment of the present invention.

Below, embodiments of a heel ankle supporter according to the present invention will be explained.

First Embodiment

A heel ankle supporter 100 has elasticity and attachable to a foot 200. As shown in FIGS. 1 to 12, the heel ankle supporter 100 is provided with a sleeve supporter 110 and a belt-type supporter 120 detachably attached to the sleeve supporter 110. The sleeve supporter 110 can cover a surface of a region including an instep 221, a sole 204, a heel 209 and an ankle 203 of the foot 200. The belt-type supporter 120 can be attached to the foot 200 on the sleeve supporter 110. The belt-type supporter 120 includes four belts respectively formed into a belt shape of a width of 4 cm to 7 cm; i.e., an ankle belt 10, a plantar heel hold belt 20, an affected-part pressing belt 30, and a posterior heel hold belt 40. Note that, illustrated examples are the heel ankle supporter 100 for a right foot.

Figure 3:
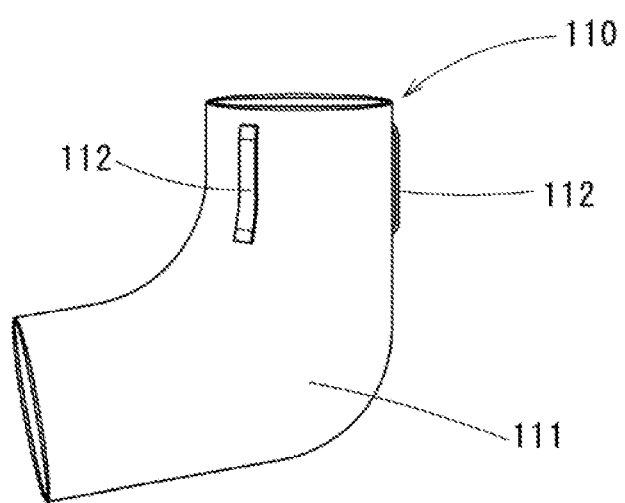
FIG. 3 It is a perspective view showing a sleeve supporter in the heel ankle supporter according to the first embodiment of the present invention.

In the sleeve supporter 110, a supporter body 111 has a shape of socks in which a tip part (a toe part) thereof is removed as shown in FIG. 3, and is formed from elastic cloth. Specifically, it is knitted cloth or woven fabric using yarn made from one of or mixed spinning of two or more, selected from synthetic resins such as polyurethane, polypropylene, nylon, polyester, polyethylene, polyethylene-terephthalate, polyamide, polycarbonate and the like. For example, yarn made of mixed spinning of polyester, polyurethane, and nylon is used. Thickness of the yarn is preferably 30 denier to 70 denier: 50 denier to 70 denier yarn is more preferable. 10 mmHg to 20 mmHg is proper for clothing pressure. The clothing pressure can be measured by an air-pack type measuring device of clothing pressure "AMI 3037-10" made by AMI Techno Co., Ltd.

It is also possible to use yarn made from acrylate resin which generates heat by absorbing moisture. Using this moisture absorbing heat generation cloth, it is possible to solve coldness and a swelling of the foot, and bad condition of autonomic nerve and chronic ischemia owing to the coldness of the foot. Accordingly, using this heel ankle supporter 100, it is expected that: sprain is prevented and an arch of the sole of the foot is improved because axes of foot joints are adjusted; gonarthrosis (knee osteoarthritis), coxarthropathy, and bow legs are prevented because the axes are improved; a low back pain (lumbago) is prevented and the coldness and the swelling (edema) is eased because a trunk of a body is supported; and damage to autonomic nerve and the other organs are reduced by easing the coldness.

Furthermore, it may have a two-layer structure of an outer material and a cloth backing. In this case, natural fibers, such as cotton and the like, which does not roughen skin can be used for the cloth backing which is in contact with the foot 200.

The sleeve supporter 110 is formed to have a size covering a part of the ankle above a medial malleolus 201 and a lateral malleolus 202 of the foot 200; specifically, covering a region a few centimeters above the malleolus 201 and 202. On the part covering the ankle 203, belt loops 112 through which the ankle belt 10 of the belt-type supporter 120 passes are formed with spacing along a circumference direction. In an example shown in FIG. 3 and the like, the belt loops 12 are provided so that two are arranged at a front side of the sleeve supporter 110 and one is arranged at a posterior side.

Figure 4:
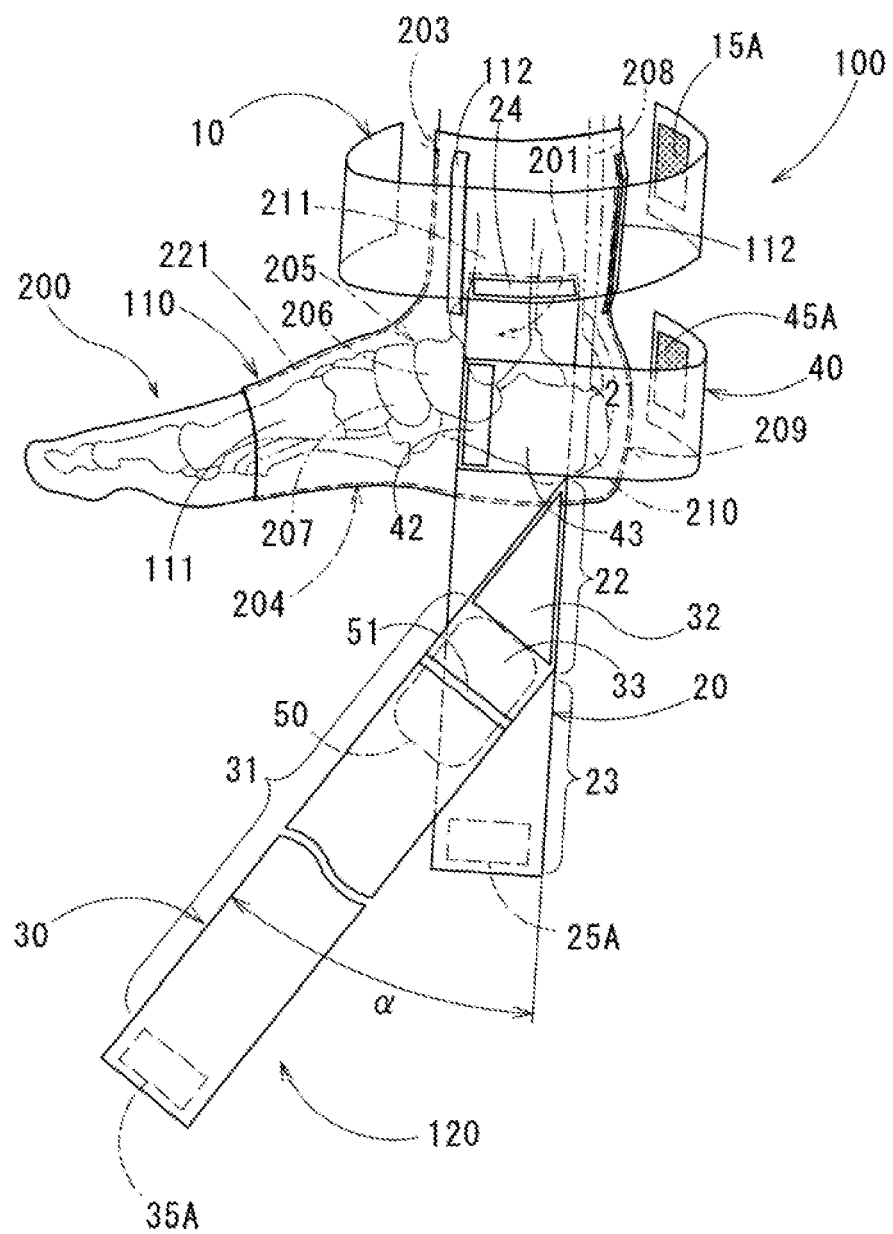
FIG. 4 It is a view showing a right foot and the heel ankle supporter of the first embodiment seen from a hallux side.
Figure 5:
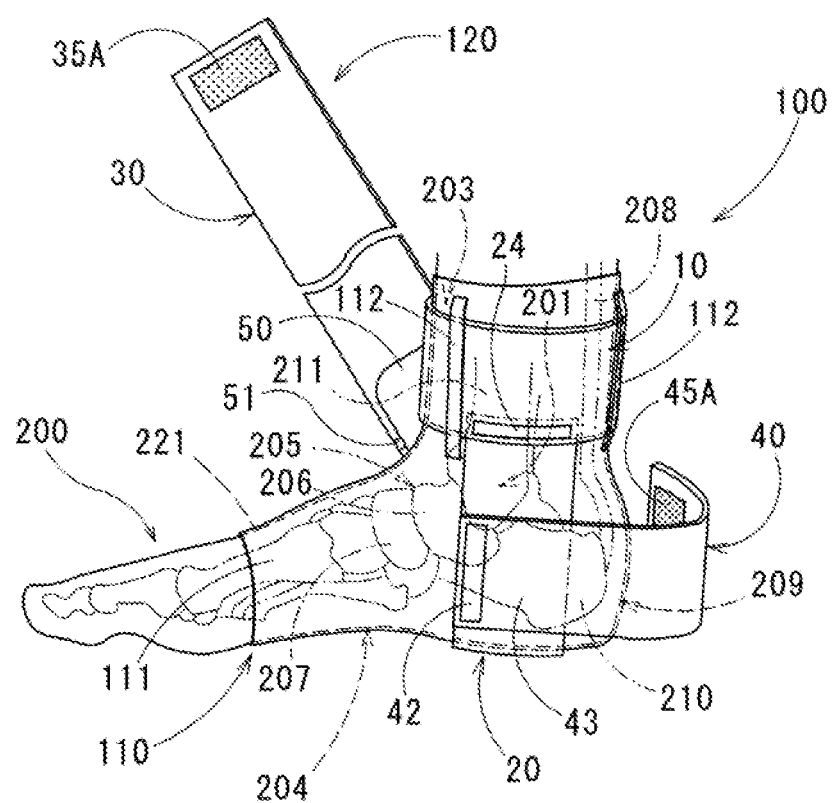
FIG. 5 It is a view showing the right foot and the heel ankle supporter of the first embodiment seen from the hallux side, in a state in which an ankle belt and a plantar heel hold belt are attached.
Figure 6:
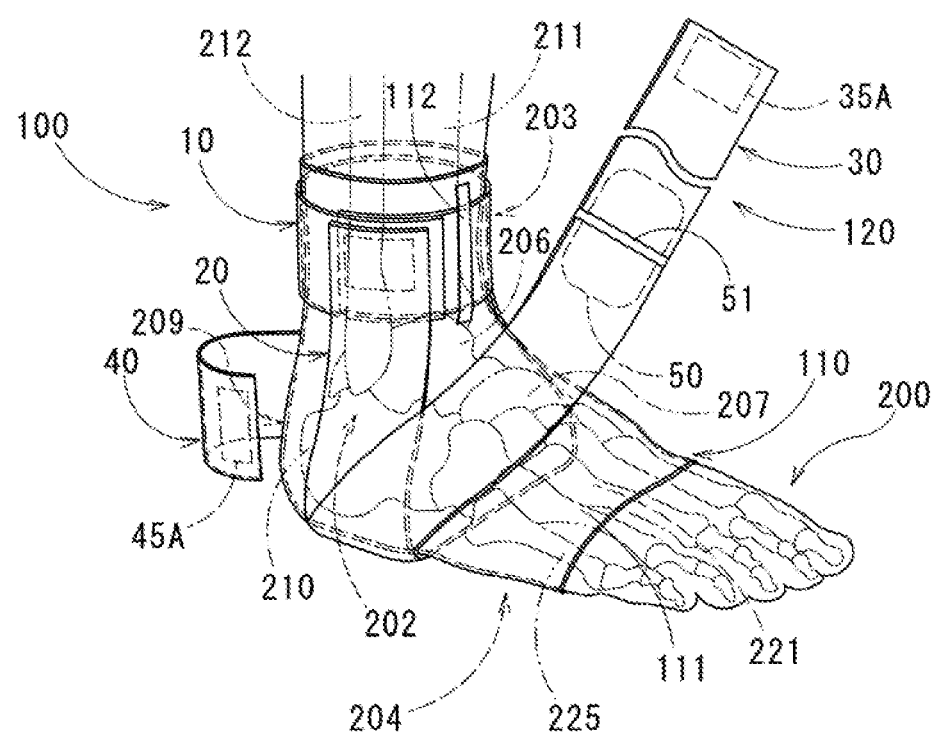
FIG. 6 It is a view showing the right foot and the heel ankle supporter of the first embodiment seen from diagonally front of a fifth toe side, in a state in which the ankle belt and a posterior heel hold belt are attached.

The ankle belt 10 of the belt-type supporter 120 is, as shown in FIGS. 4 to 6, configured to be fixable to the ankle 203 by winding around the ankle 203 above the medial malleolus 201 and the lateral malleolus 202 of the foot 200.

The plantar heel hold belt 20 is fixed to the ankle belt 10 at one end of a longitudinal direction; extending in a perpendicular direction to the ankle belt 10 from the one end to the other end toward a part below the ankle belt 10 as shown in FIGS. 1, 2, and 4 to 6. The plantar heel hold belt 20 includes: an inner cover part 21 which is connected to the ankle belt 10 and can cover the vicinity of the medial malleolus 201; a plantar cover part 22 which is connected to the inner cover part 21 and can cover the sole 204 at a front part of a calcaneus bone 210; and an outer cover part 23 which is connected to the plantar cover part 22 and can cover the vicinity of the lateral malleolus 202. The plantar heel hold belt 20 is fixed to the ankle belt 10 on an inner surface at a lower side of a width direction thereof by a fixing part 24 provided at one end. The plantar heel hold belt 20 is fixed to an outer surface of the ankle belt 10 disposed at an outside of the foot 200 at the other end so as to be fixed to the foot 200 with passing through the sole 204 of the foot in an extended condition.

Figure 2:
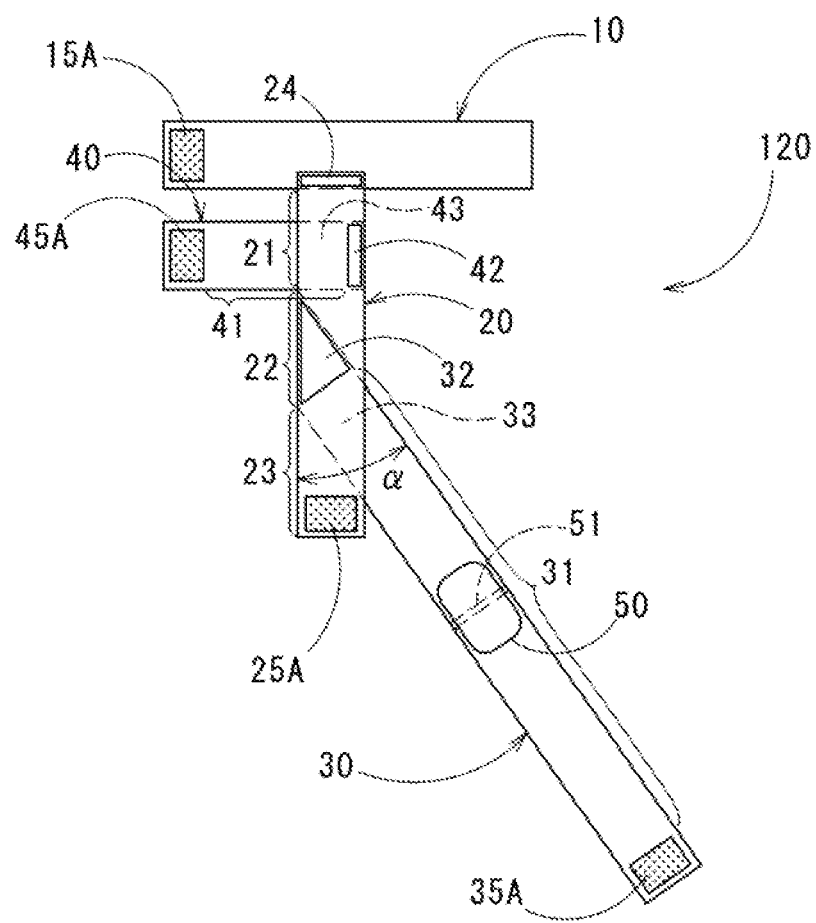
FIG. 2 It is a plan view showing an inner surface of the belt-type supporter shown in FIG. 1.

As shown in FIGS. 1, 2, and 4, the affected-part pressing belt 30 is fixed to the plantar heel hold belt 20 at one end of a longitudinal direction and has a pressing part 31. The pressing part 31 is provided so as to extend from the one end to the other end in a diagonal direction apart from the plantar heel hold belt 20 with a crossing angle α, i.e., 30 to 60°, preferably 40°. The pressing part 31 is wound in a direction toward inside the foot 200 from the outside of the foot 200, passing on an instep side of the foot 200, so as to cover an affected part. The affected-part pressing belt 30 is fixed at the other end to either one of the outer surfaces of the ankle belt 10, the plantar heel hold belt 20, or the affected-part pressing belt 30 at an intermediate part in a longitudinal direction thereof so as to cover the affected part in an extended condition and be fixed to the foot 200.

The one end of the affected-part pressing belt 30 is provided so as to cross the plantar cover part 22 of the plantar heel-holed belt 20 as shown in FIGS. 1, 2, and 4. The affected-part pressing belt 30 is fixed to the outer surface of the plantar cover part 22 at a position of a base end side of the cross part, i.e., at a position over a latter part in a width direction, and on an upper side in a longitudinal direction of the plantar cover part 22. Therefore, at the one end of the affected-part pressing belt 30, formed are a fixing part 32 fixed to the plantar cover part 22 and an overlapped part 33 provided to be connected to the fixing part 32 and overlapped on the outer surface of the plantar cover part 22 at a position of a former part in the width direction and on a lower side in the longitudinal direction of the plantar cover part 22. In this case, the fixing part 32 is formed to be a right-angled triangle in a plan view as shown in FIGS. 1 and 2: a hypotenuse thereof is formed along a side edge of the plantar heel hold belt 20: and an end edge (a narrow side) thereof is provided to be perpendicular to the longitudinal direction of the affected-part pressing belt 30.

On the inner surface of the affected-part pressing belt 30, a pressing part 50 pressing the affected part is disposed. The pressing pad 50 is provided from a member having elasticity in a thickness direction (a pressing direction) as a whole. It can be formed, for example, by filling cushions in which elastic fibers such as nylon and the like having elasticity against bending are gathered (in a point contact state) in three dimensions in a bag made of cloth. In this case, since the cushions have elasticity, it is possible to press the affected part evenly with dispersing the pressing forth. Since the cushions have fiber structure, the air can pass through, so that it is possible to prevent the affected part from being damp. The pressing pad 50 includes a holding belt 51 spanning the affected-part pressing belt 30 in the width direction so as to be movable along the longitudinal direction of the affected-part pressing belt 30. Consequently, the pressing pad 50 can be moved in a wide span of the affected-part pressing belt 30 as far as the overlapped part 33 of a base (a root) of the pressing part 31.

As shown in FIGS. 4 to 6, one end of a longitudinal direction of the posterior heel hold belt 40 is fixed to the plantar heel hold belt 20 below the medial malleolus 201 and the lateral malleolus 202: the posterior heel hold belt 40 is provided to extend backward from the plantar heel hold belt 20 and to be parallel to the ankle belt 10 (i.e., perpendicular to the length direction of the plantar heel hold belt 20, and has a posterior cover part 41 which can cover a back of the vicinity of the calcaneus bone. The posterior heel hold belt 40 is fixed to the outer surface at the former part in the width direction of the plantar heel hold belt 20 by a fixing part 42 provided at one end. On one end of the posterior heel hold belt 40, formed are the fixing part 42 fixed to the outer surface of the plantar heel hold belt 20 and an overlapped part 43 connected to the fixing part 42 and overlapped on the outer surface at the latter part in the width direction of the plantar heel hold belt 20.

In this case, the fixing part 42 is formed on whole width of the posterior heel hold belt 40 with a width of ⅓ to ¼ of the width of the plantar heel hold belt 20. Accordingly, the overlapped part 43 is overlapped on ⅔ to ¾ of the width of the plantar heel hold belt 20. The width of the overlapped part 43 is preferably at least a half (½) or larger of the width of the plantar heel hold belt 20. The posterior heel hold belt 40 is provided by being fixed at the other end to the outer surface of the outer cover part 23 disposed at the outside of the foot 200: so that it is fixable to the heel 209 of the foot 200 with covering the back part of the calcaneus bone 210 in the extended state.

The heel ankle supporter 100 is made from elastic material such as resin and the like as a whole; and the inner surface in which skin touches is covered by material having water absorbency and hygroscopicity such as non-woven fabric. Hook surface parts 15A, 25A, 35A, and 45A of hook and loop fasteners are provided on inner surfaces of the ankle belt 10, the plantar heel hold belt 20, the affected-part pressing belt 30, and the posterior heel hold belt 40 at the other ends thereof, respectively. Loop surface parts corresponding to the hook surface parts 15A, 25A, 35A, and 45A are respectively provided at somewhere of the outer surfaces of the ankle belt 10, the plantar heel hold belt 20, the affected-part pressing belt 30, and the posterior heel hold belt 40. In the heel ankle supporter 100 of the present embodiment, the loop surface parts are provided on the whole of the outer surfaces of the ankle belt 10, the plantar heel hold belt 20, the affected-part pressing belt 30 and the posterior heel hold belt 40. The loop surface parts of the heel ankle supporter 100 are provided on the whole outer surface, so that illustration is omitted.

The belt-type supporter 120 is formed from polyester resin, polyurethane resin, polyolefinic resin, polyamide resin and the like, and have elasticity. In this case, comparing the belt-type supporter 120 and the aforementioned sleeve supporter 110, the sleeve supporter 110 is more elastic: material showing larger extension than that of the respective belts 10, 20, 30 and 40 of the belt-type supporter 120 is used for the sleeve supporter 110. When the sleeve supporter 110 and the respective belts 10, 20, 30 and 40 of k120 are stretched by the same force, the extension of the sleeve supporter 110 is larger than that of the belt-type supporter 120, 50% stretching load of the sleeve supporter 110 is preferably 7 N or larger and 10 N or smaller. "50% stretching load" is a load when stretching it to a length of 50% extension, conforming a measuring method of stretching load regulated by JIS L 1096.

A wearing method of the heel ankle supporter 100 structured above will be explained.

First, as shown in FIG. 4, the ankle belt 10 of the belt-type supporter 120 is passed through one belt loop 112 provided at the posterior side (the heel side) among the belt loops 112 of the sleeve supporter 110; then the sleeve supporter 110 is attached to the foot 200 so that the sleeve supporter 110 covers the surface of the region including the instep 221, the sole 204, the heel 209 and the ankle 213 of the foot 200. The ankle belt 10 of the belt-type supporter 120 may be passed through rear ones of the belt loops 112 after attaching only the sleeve supporter 110 to the foot 200.

Then, winding the ankle belt 10 around immediately above the medial malleolus 201 and the lateral malleolus 202; passing the ankle belt 10 through the two belt loops 112 disposed at the front of the sleeve supporter 110 as necessary; fasten the hook surface part 15A of the inner surface onto the loop surface part of the outer surface, so that it is attached to the ankle 203 as shown in FIG. 5 and FIG. 6. Thereby being attached the ankle belt 10 to the ankle 203 on the sleeve supporter 110. At this time, a position of the ankle belt 10 is adjusted so that the inner cover part 21 of the plantar heel hold belt 20 covers the medial malleolus 201 and extends downward from the ankle belt 10.

Next, while extending the plantar heel hold belt 20 from the medial malleolus 201 side (a first finger side) to the lateral malleolus 202 side (a fifth finger side) through the sole 204 of the foot 200, the plantar heel hold belt 20 is attached and fixed to the foot 200 by fasten the hook surface part 25A at the inner surface of the plantar heel hold belt 20 onto the outer surface (the loop surface part) of the ankle belt 10. Although sizes of the foot 200 are different depending on person, arrangement of the ankle belt 10 and the plantar heel hold belt 20 can be finely adjusted corresponding to the size of the foot 200 individually since the ankle belt 10 and the plantar heel hold belt 20 are attached to the foot 200 by winding belt-shaped belts round. Accordingly, the heel-ankle support 100 can be stably attached to the individual foot 200.

As described above, after fixing the ankle belt 10 and the plantar heel hold belt 20 to the foot 200, the affected-part pressing belt 30 and the posterior cover belt 40 extending from the plantar heel hold belt 20 are attached and fixed. Thereby attaching and fixing the belt-type supporter 120 to the foot 200 on the sleeve supporter 110. An attachment order of the affected-part pressing belt 30 and the posterior heel hold belt 40 is reversed in accordance with a purpose of use of the heel ankle supporter 100.

For example, if the heel ankle supporter 100 is worn in order to prevent inversion sprain of the ankle and to ease symptom of plantar fasciitis and calcaneitis proceeded from the inversion sprain, the posterior heel hold belt 40 is attached after attaching the affected-part pressing belt 30.

Figure 7:
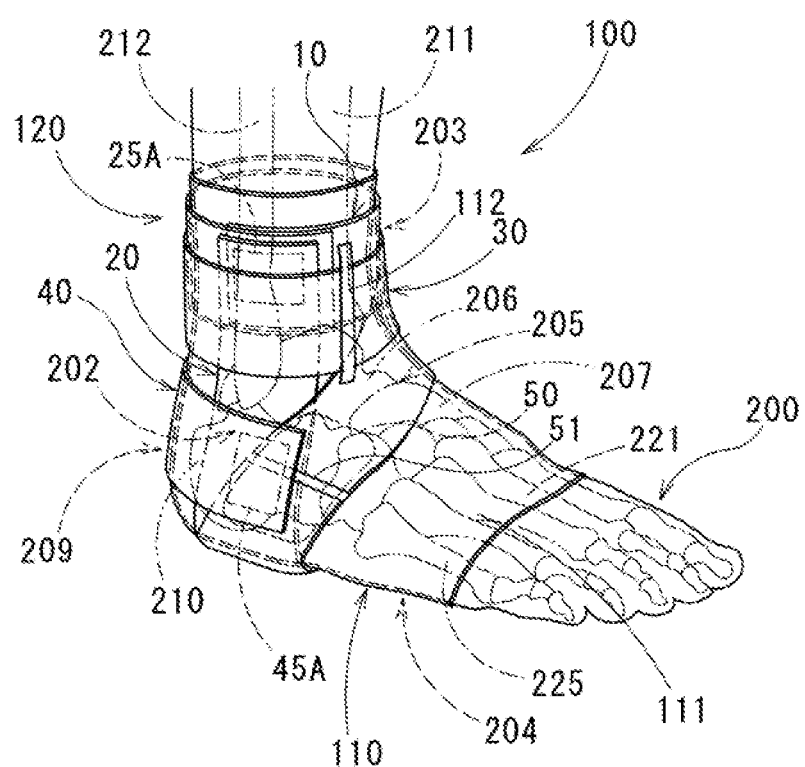
FIG. 7 It is a view showing the right foot and the heel ankle supporter of the first embodiment seen from diagonally front of the fifth toe side, and showing an example of an attachment pattern of the heel ankle supporter to the foot.

Specifically, as shown in FIG. 7, the affected-part pressing belt 30 extending from the plantar heel hold belt 20 is further stretched toward the upper inner side (diagonally upward of the first finger) so as to press the pressing pad 50 to the affected part (a ligament) in which inflammation (injury) is occurred and to be extended from ahead of a talus 206 along a Chopart joint 205, and wound around the ankle 203 on an outer surface of a tibia (shin bone) 211 (above the medial malleolus 201), an Achilles' tendon 208 (refer to FIG. 5 and so forth) and an outer surface of of a fibula (a calf bone) 212. Then, the hook surface part 35A of the inner surface of the other end part of the affected-part pressing belt 30 is fixed to any loop surface part of the outer surface of the heel ankle supporter 100, somewhere of the outer surface of the ankle belt 10 or the planter heel hold belt 20, or somewhere of the outer surface of a part of the affected-part pressing belt 39 in a wound state.

At this time, an extending angle of the affected-part pressing belt 30 to the plantar heel hold belt 20 can be easily fine-adjusted, because the overlapped part 33 is provided at one end part of the affected-part pressing belt 30 so as to be connected to the fixing part 32 at a crossing part to the plantar heel hold belt 20 (refer to FIG. 4 and so forth). It is possible to press the plantar cover part 22 of the plantar heel hold belt 20 to the sole 204 by the overlapped part 33; and the plantar heel hold belt 20 can be maintained to be stably fixed to the foot 200.

Accordingly, as shown in FIG. 7, pressing and covering the affected part by the pressing pad 50, it is possible to press the talus 206 backward by the affected-part pressing belt 30; and the affected-part pressing belt 30 can be suitably attached.

After fixing the affected-part pressing belt 30, the posterior heel hold belt 40 extending from the plantar heel hold belt 20 between the ankle belt 10 and the affected-part pressing belt 30 is stretched round from the inside to the outside of the foot 200, passing through the back part in the vicinity of the calcaneus bone 210, and fixed below the medial malleolus 201 and the lateral malleolus 202. As a result, it is possible to draw the calcaneus bone 210 entering inside the foot 200 to the outside, so that the calcaneus bone 210 can be fixed outside the foot. Therefore, fixing the posterior heel hold belt 40 to the heel 209, the adducted calcaneus bone 210 can be corrected and the calcaneus bone 210 can be prevented from entering inside the foot 200, so that correction of the adducted calcaneus bone 210 and prevention of adduction of the calcaneus bone 210 can be rigidly performed.

The posterior heel hold belt 40 is provided with the overlapped part 43 connected to the fixing part 42 provide at one end of the posterior heel hold belt 40 and overlapped on a rear half in the width direction of the outer surface of the plantar heel hold belt 20 (refer to FIG. 5 and the like): the calcaneus bone 210 can be stable and the foot 200 can be rigidly pressed from the inside to the outside by pressing the plantar heel hold belt 20 to the inside of the foot 200 by the overlapped part 43.

Furthermore, when attaching the posterior heel hold belt 40, the ankle belt 10 and the plantar heel hold belt 20 are stably fixed to the foot 200: so that the posterior heel hold belt 40 can be stably fixed. Since the affected-part pressing belt 30 is diagonally extended forward from the plantar heel hold belt 20 and fixed to the posterior heel hold belt 40 extended to the posterior of the foot 200 from the plantar heel hold belt 20: when the posterior heel hold belt 40 is fixed to the heel 209, tension force on the plantar heel hold belt 20 can be balanced between the affected-part pressing belt 30 and the posterior heel hold belt 40, so that the posterior heel hold belt 40 can be rigidly and stably fixed to the heel 209. Accordingly, it is possible to reliably hold the calcaneus bone 210 at a stable position by the posterior heel hold belt 40.

It is also possible to use the heel ankle supporter 100 for treating bifurcate ligament injury and fifth metatarsal bone sprain. Also in this case, as shown in FIGS. 8 and 9, after attaching the affected-part pressing belt 30, the posterior heel hold belt 40 is attached.

Figure 8:
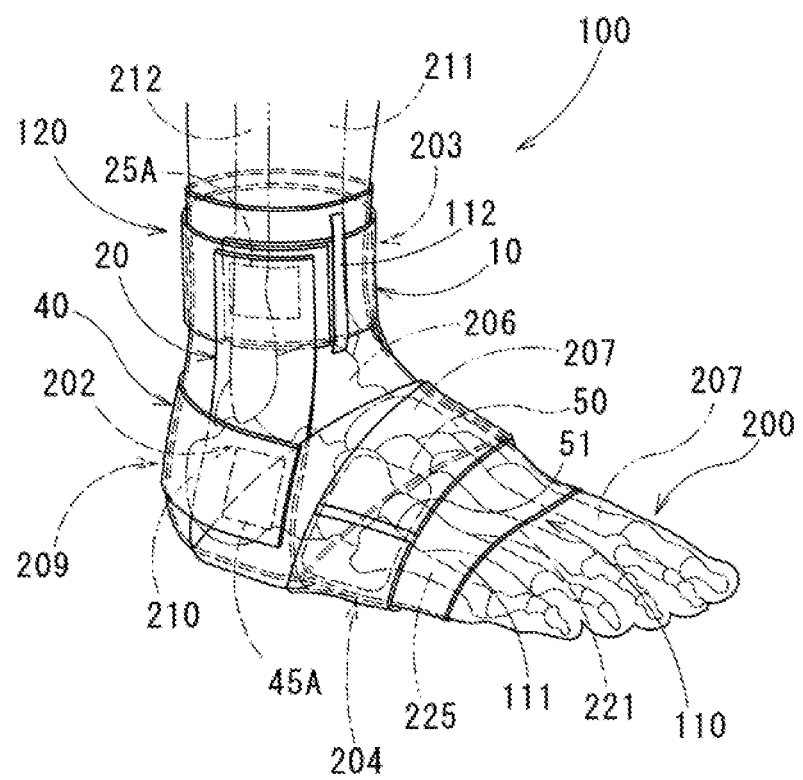
FIG. 8 It is a view showing the right foot and the heel ankle supporter of the first embodiment seen from diagonally front of the fifth toe side, and showing an example of an attachment pattern of the heel ankle supporter to the foot.
Figure 9:
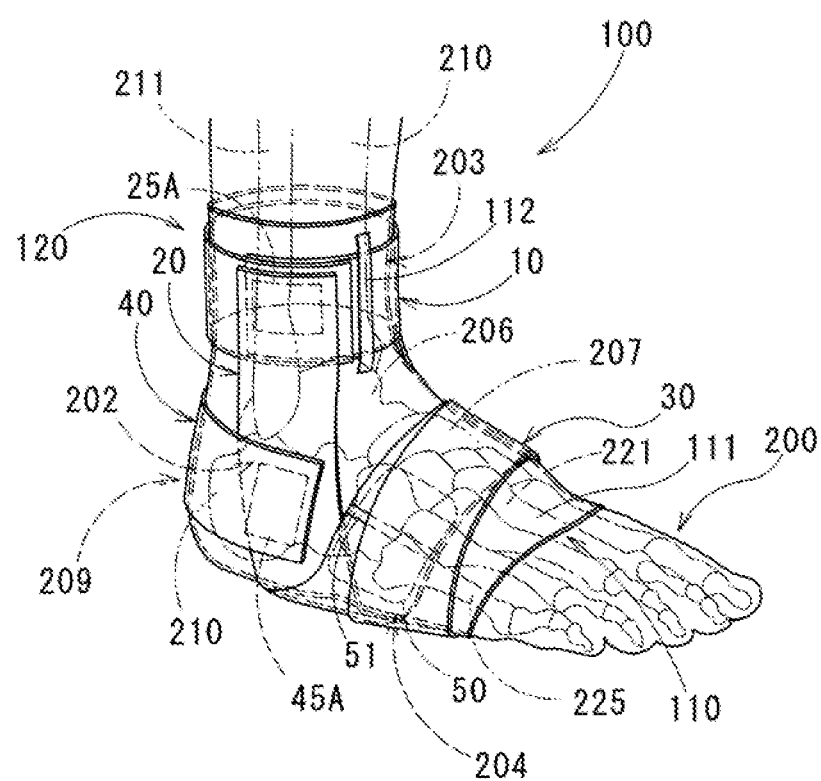
FIG. 9 It is a view showing the right foot and the heel ankle supporter of the first embodiment seen from diagonally front of the fifth toe side, and showing an example of an attachment pattern of the heel ankle supporter to the foot.

Specifically, as shown in FIGS. 8 and 9, while stretching the affected-part pressing belt 30 extended from the plantar heel hold belt 20, the pressing pad 50 is put to the affected part in which inflammation (injury) is developed (a ligament or a fifth metatarsal bone 225), and the affected-part pressing belt 30 is wound round the foot 200. Then, the hook surface part 35A on the inner surface of the affected-part pressing belt 30 at the other end is attached and fixed on somewhere of the loop surface of the outer surface of the heel ankle supporter 100. Thereby quietly maintaining the affected part. Note, winding positions of the affected-part pressing belt 30 are different between FIGS. 8 and 9. As especially shown in FIG. 8, as results of covering the instep 221 and the sole 204 of the foot 200 with one round and adding a tension force on a navicular bone 207 and a transverse arch (an arch between a root of a fifth toe and a root of a first toe) of the foot 200, the talus 206 is protected by a main function of the longest belt (the affected-part pressing belt 30): and furthermore, disorder of the transverse arch of the foot 200 can be improved: and a shock on foot joints and the plantar by jumping or running can be absorbed, by adding a force of lifting the arch.

Figure 10:
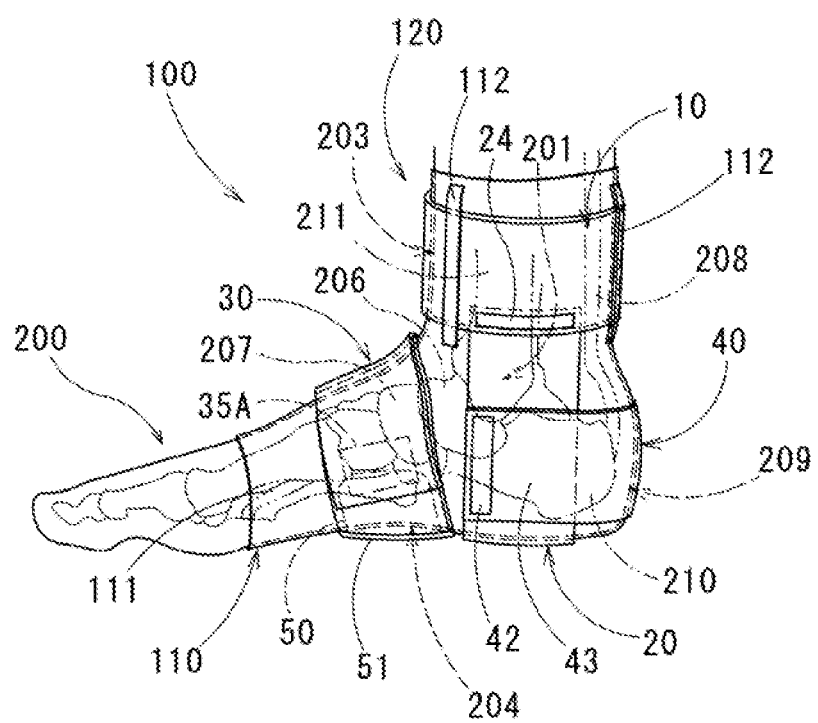
FIG. 10 It is a view showing the right foot and the heel ankle supporter of the first embodiment seen from diagonally front of the hallux side, and showing an example of an attachment pattern of the heel ankle supporter to the foot.

Moreover, the heel ankle supporter 100 can be used for treatment of inflammation of the navicular bone. For this case, as shown in FIG. 10, the pressing pad 50 is put to the sole 204 in the vicinity of the navicular bone 207, and the affected-part pressing belt 30 is stretched and wound round the foot 200. Then the hook surface part 35A on the inner surface of the other end of the affected-part pressing belt 30 is fixed on the loop surface part on the outer surface of the affected-part pressing belt 30.

Thus the navicular bone 207 can be lifted by attaching the affected-part pressing belt 30 to the foot 200.

Figure 11:
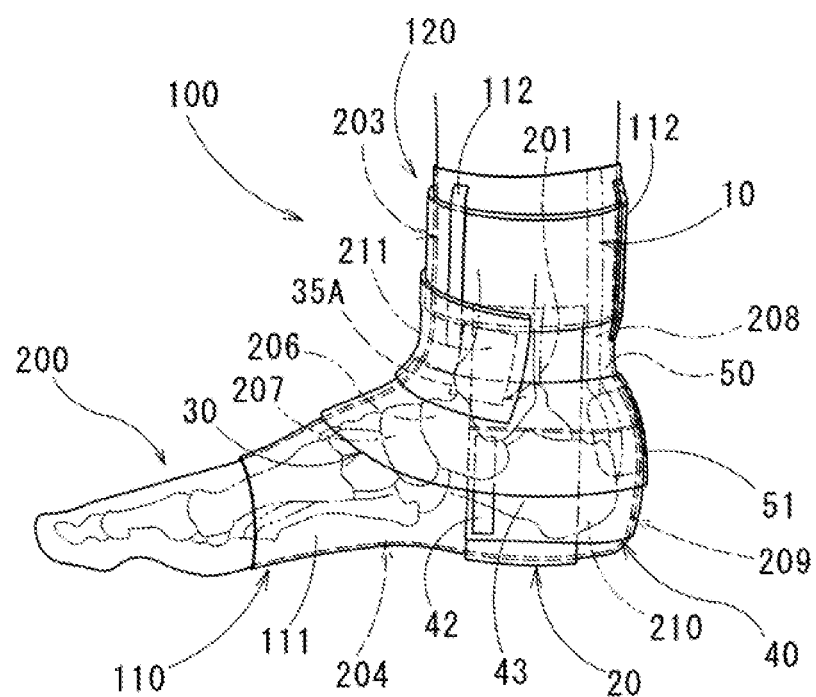
FIG. 11 It is a view showing the right foot and the heel ankle supporter of the first embodiment seen from diagonally front of the hallux side, and showing an example of an attachment pattern of the heel ankle supporter to the foot.

The heel ankle supporter 100 can be used also for treatment of Achilles tendonitis. For example, for treatment of Achilles enthesitis, as shown in FIG. 11, the calcaneus bone 210 is previously stabilized by attaching the posterior heel hold belt 40, and then the affected-part pressing belt 30 is attached on the posterior heel hold belt 40. At this time, the pressing pad 50 is put on entheses of the Achilles' tendon 208, and the affected-part pressing belt 30 is wound round the foot 200 with stretching. Then, the hook surface part 35A at the other end of the affected-part pressing belt 30 is put on the loop surface part on the outer surface of the heel ankle supporter 100 so as to be fixed, so that the entheses of the Achilles' tendon 208 can be pressed.

Figure 12:
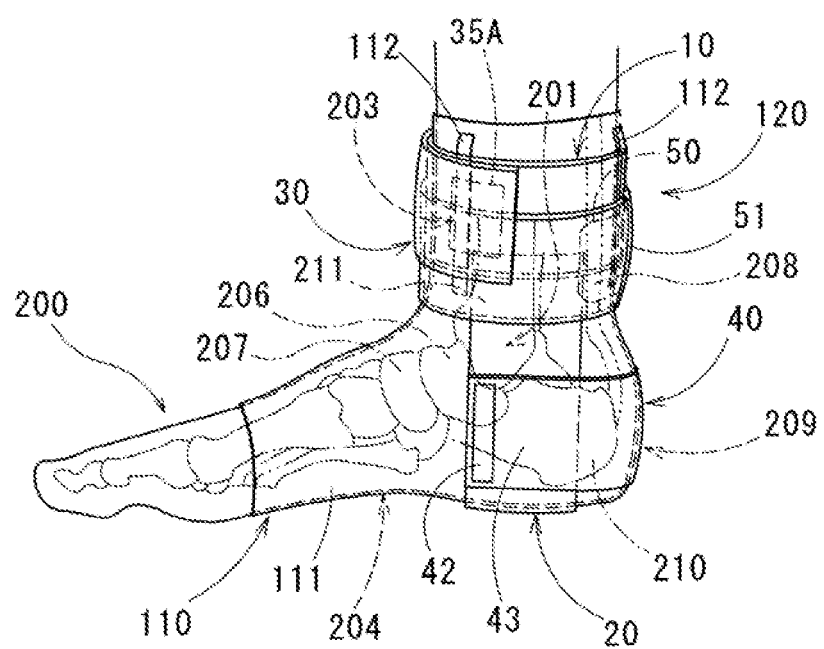
FIG. 12 It is a view showing the right foot and the heel ankle supporter of the first embodiment seen from diagonally front of the hallux side, and showing an example of an attachment pattern of the heel ankle supporter to the foot.

For a treatment of Achilles parenchymatitis, as shown in FIG. 12, the pressing pad 50 is put on the Achilles' tendon 208, and the affected-part pressing belt 30 is wound round the ankle 203 with stretching. Then, the hook surface part 35A at the other end of the affected-part pressing belt 30 is put onto the loop surface part of the outer surface of the heel ankle supporter 100 so as to be fixed, so that the Achilles' tendon 208 can be pressed.

In any of cases shown in FIGS. 7 to 12, by the posterior heel hold belt 40, the adducted calcaneus bone 210 can be corrected, and the calcaneus bone 210 can be prevented from moving to the inside of the foot 200; so that the correction of the adducted calcaneus bone 210 and the prevention of the adduction of the calcaneus bone 210 can be rigidly performed. Accordingly, the other tissues are not drawn inward, it is possible to stably protect or treat the affected part.

As described above, the heel ankle supporter 100 can be stably attached to the individual foot 200 without individual difference, so that the calcaneus bone 210 can be stably held by the posterior heel hold belt 40. Therefore, it is reliably possible to protect and treat the affected part with preventing and correcting transverse deviation of the calcaneus bone 210. In this case, since the belt-type supporter 120 is overlapped on the sleeve supporter 110 so as to be fixed to the foot 200, it is possible to fix the foot joint to a suitable position without deviation, and moreover, it is easy to handle. The belt-type supporter 120 is not directly in contact with skin and is not easily dislocated; skin irritation, scratches and the like by the dislocation are prevented, so that it can be stably used.

Moreover, since the sleeve supporter 110 is elastic, it is possible to press moderately on the overall surface of the region including the instep 221, the sole 204, the heel 209 and the ankle 203 of the foot 200: a pressing force of the belt-type supporter 120 is transmitted to the vicinity of the parts in which the belts of the belt-type supporter 120 are attached via the sleeve supporter 110, it is possible to support broadly muscles not only bones. Therefore, it is possible to prevent muscles from excessive stretching when walking or the like of a person wearing the heel ankle supporter 100. On the other hand, the pressing force of the sleeve supporter 110 is small; the foot 200 is not excessively pressed, so that moderate action of the muscles is not prevented.

It is possible to cover or press the affected parts of the various injuries by the affected-part pressing belt 30, so that flexible treatments are possible such as correction of bones and joints around the ankle 203 and easing of symptoms of the injuries.

Second Embodiment

Figure 13:
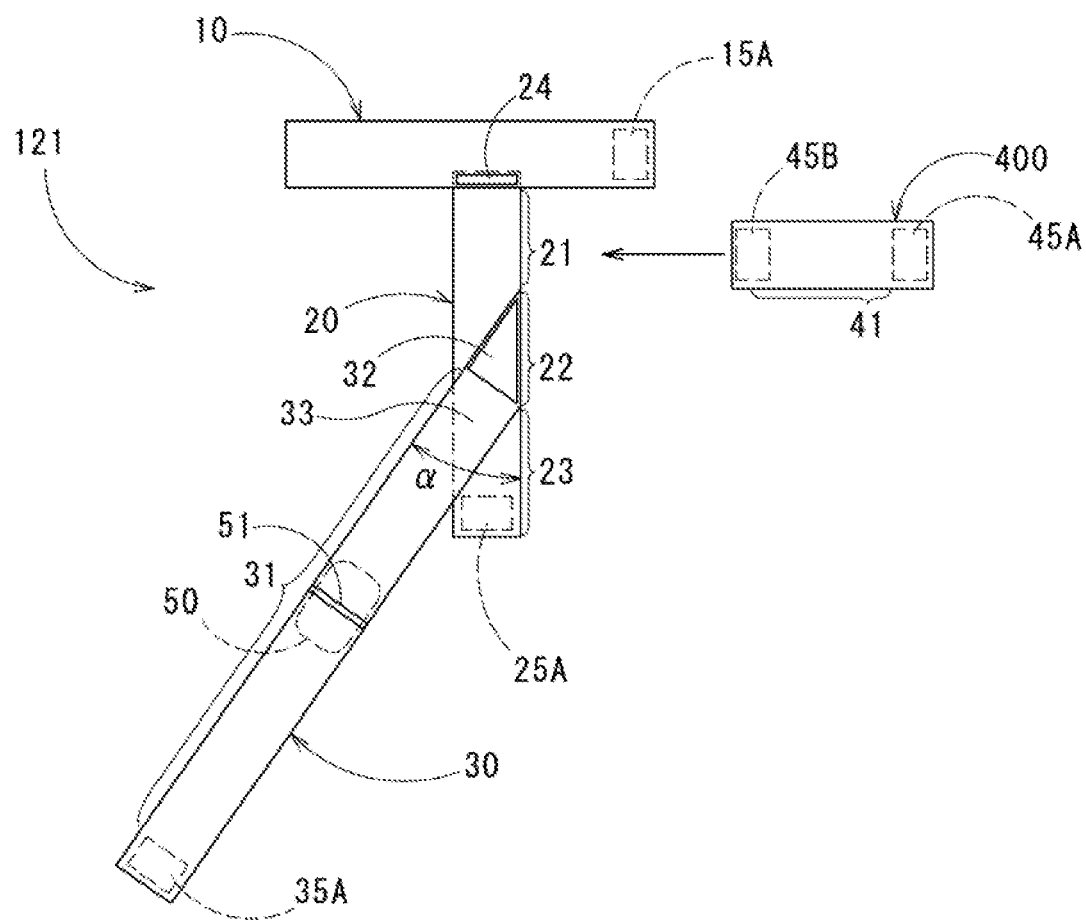
FIG. 13 It is a plan view showing an outer surface of a belt-type supporter in a heel ankle supporter according to a second embodiment of the present invention.
Figure 14:
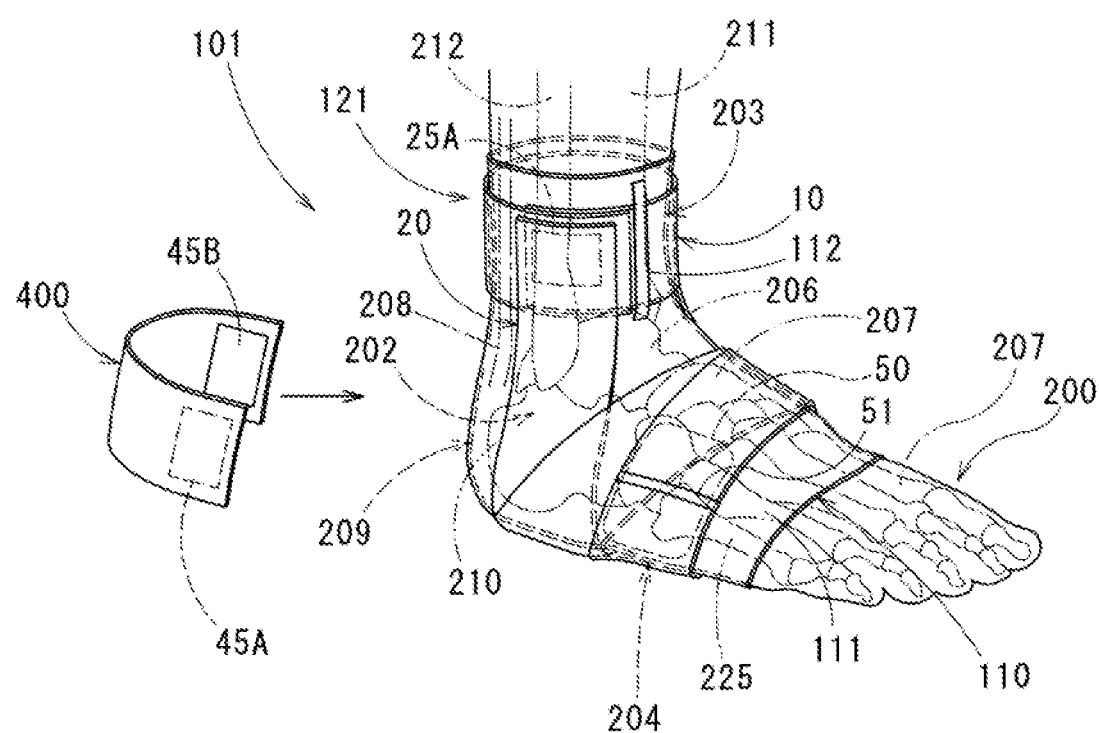
FIG. 14 It is a view showing a right foot and the heel ankle supporter of the second embodiment seen from diagonally front of a fifth toe side, in a state in which before a plantar heel hold belt is attached.
Figure 15:
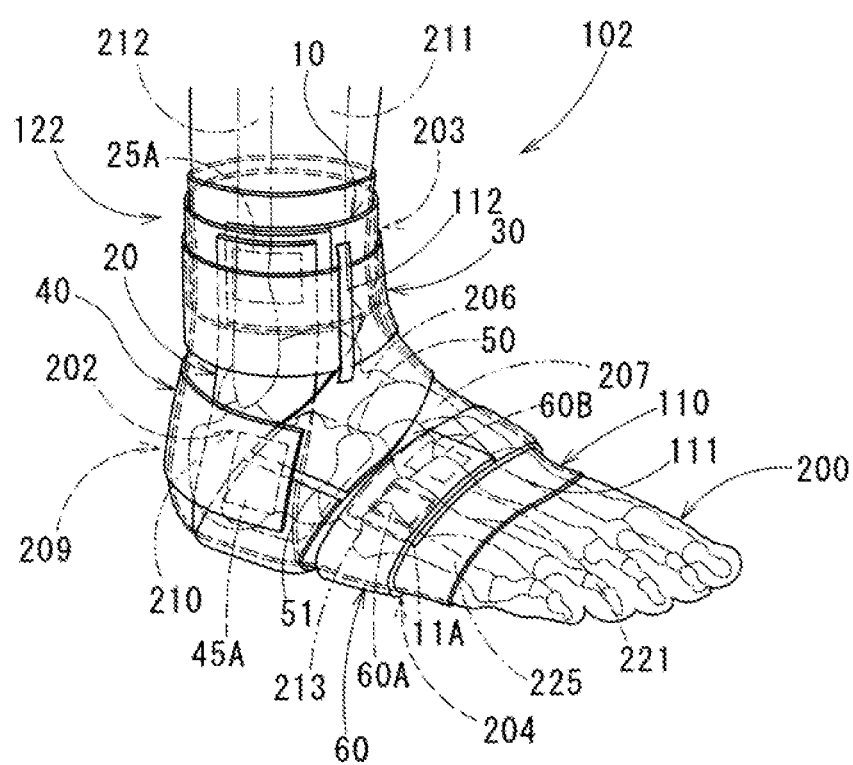
FIG. 15 It is a view showing a right foot and a heel ankle supporter of a third embodiment of the present invention seen from diagonally front of a fifth toe side, and showing an example of an attachment pattern of the heel ankle supporter to the foot.

A heel ankle supporter 101 of a second embodiment is one in which a posterior heel hold belt 400 is detachable in a belt-type supporter 121 as shown in FIGS. 13 and 14.

Hook surface parts 45A and 45B of a hook and loop fastener are provided on an inner surface at both ends of the posterior heel hold belt 400 so as to be put on a loop surface part on an outer surface of the plantar heel hold belt 20. It is the same structure as that of the heel ankle supporter 100 of the first embodiment except for a structure in which the posterior heel hold belt 400 is detachable; the same elements are denoted by the same reference symbols, and an explanation thereof is abbreviated (a third embodiment described below will be the same).

In the heel ankle supporter 101, after wearing the sleeve supporter 110 to the foot 200, the ankle belt 10 of the belt-type supporter 121 is fixed to the ankle 203; the plantar heel hold belt 20 is stretched along the medial malleolus 201, the sole 204, and the lateral malleolus 202 of the foot 200; and the hook surface part 25A on the inner surface is put on the outer surface of the ankle belt 10 (the loop surface part). Then, while stretching the affected-part pressing belt 30, the hook surface part 35A on the inner surface of the end is put on any of the loop surface parts of the outer surface of the ankle belt 10 or the outer surface of a part in which the affected-part pressing belt 30 is wound before so as to fix the affected-part pressing belt 30.

If it is necessary to fix a bone part (the calcaneus bone 210) of the heel 209, the posterior heel hold belt 400 is further attached. In this case, the posterior heel hold belt 400 is fixed by: putting one end of the posterior heel hold belt 400 on either one of the plantar heel hold belt 20 or the affected-part pressing belt 30, or the outer surface of a part spanning across these parts: passing the posterior heel hold belt 400 through the back of the heel 209: and putting the other end of the posterior heel hold belt 400 on either one of the plantar heel hold belt 20 or the affected-part pressing belt 30, or the outer surface of a part spanning across these parts.

If it is necessary to fix the Achilles' tendon 208 above the calcaneus bone 210, the posterior heel hold belt 400 is attached at a position above the calcaneus bone 210 and wound round the Achilles' tendon 208 so as to fix.

If it is not necessary to fix the heel 209 or the Achilles' tendon 208, the posterior heel hold belt 400 does not have to be attached.

As described above, since the posterior heel hold belt 400 is detachable, it is possible to use the posterior heel hold belt 400 in accordance with a symptom of a patient: the posterior heel hold belt 400 can be fixed at a suitable position in this case.

Third Embodiment

In a heel ankle supporter 102 of a third embodiment, a belt-type supporter 122 is provided with an instep hold belt 60 pressing an instep 221 of the foot 200. The instep hold belt 60 is detachably provided at an end of the sleeve supporter 110.

The instep hold belt 60 is wound around the instep 221 and the sole 204 of the foot 200 with one or more rounds so as to fix; an overall outer surface thereof is provided with a loop surface part, and hook surface parts 60A and 60B are provided on an inner surface at both ends, as same in the belts in the above-mentioned embodiments. The sleeve supporter 110 has a loop surface part 11A on a part of the outer surface at the end. Putting the hook surface part 60A provided at one end on the loop surface part 11A of the sleeve supporter 110; winding around the instep 221 of the foot 200 with one or more rounds, and then putting the hook surface part 60B provided at the other end on the loop surface part on the outer surface thereof, so that the instep hold belt 60 is fixed. The loop surface part 11A is formed not only on a part, but the loop surface part may be formed on a broad part covering the overall outer surface of the sleeve supporter 110 or the instep 221.

The instep hold belt 60 can be used for a case in which healing of injury at the instep 221 or shock mitigation at the instep 221 would be necessary. Especially, it is suitable for reducing a pain of Lisfranc joints 213 between bones of the instep 221 of the foot 200 and the respective five metatarsals (bones of toes).

Fourth Embodiment

Figure 16:
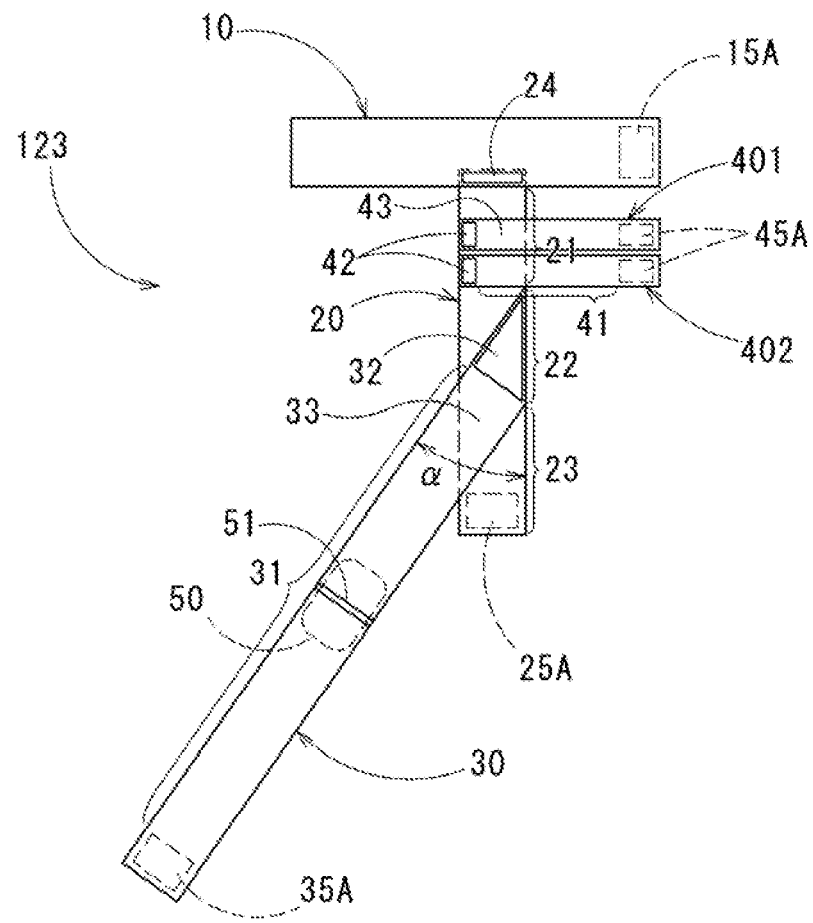
FIG. 16 It is a plan view showing an outer surface of a belt-type supporter in a heel ankle supporter according to a fourth embodiment of the present invention.
Figure 17:
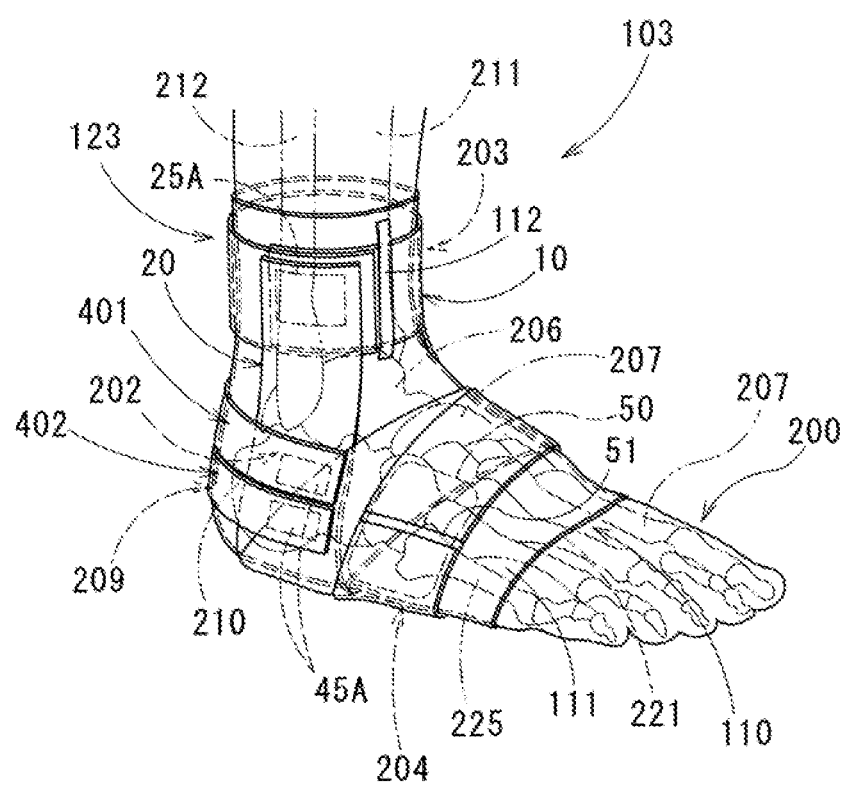
FIG. 17 It is a view showing a right foot and the heel ankle supporter of the fourth embodiment seen from diagonally front of a fifth toe side, and showing an example of an attachment pattern of the heel ankle supporter to the foot.
Figure 18:
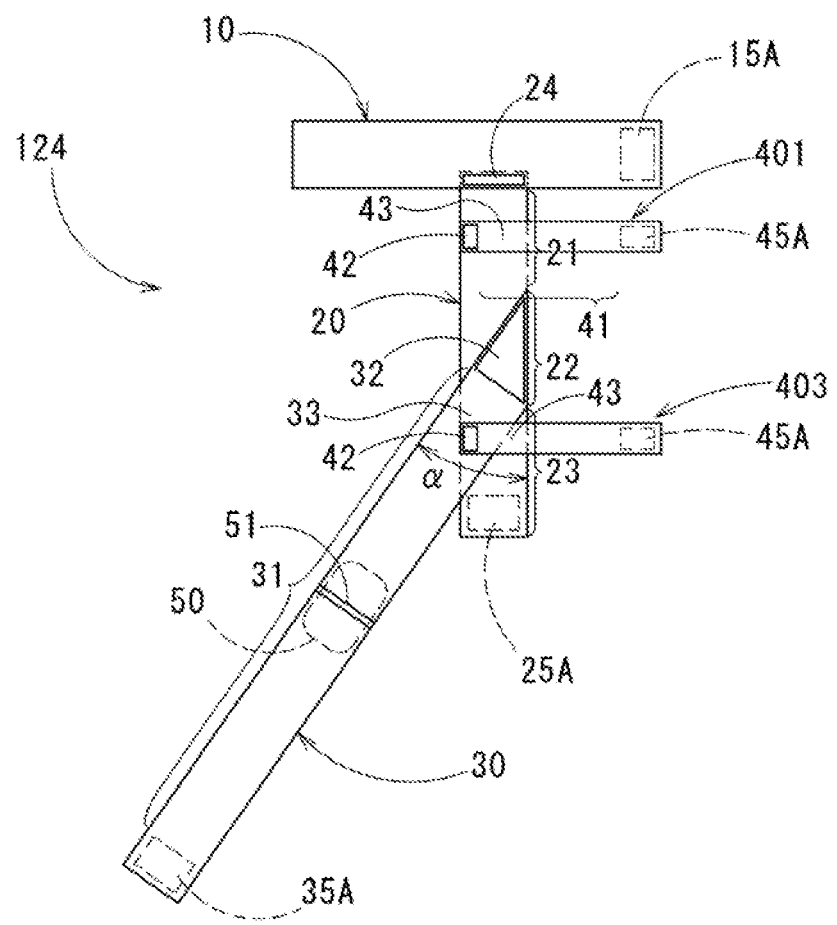
FIG. 18 It is a plan view showing an outer surface of a belt-type supporter in a heel ankle supporter according to a fifth embodiment of the present invention.
Figure 19:
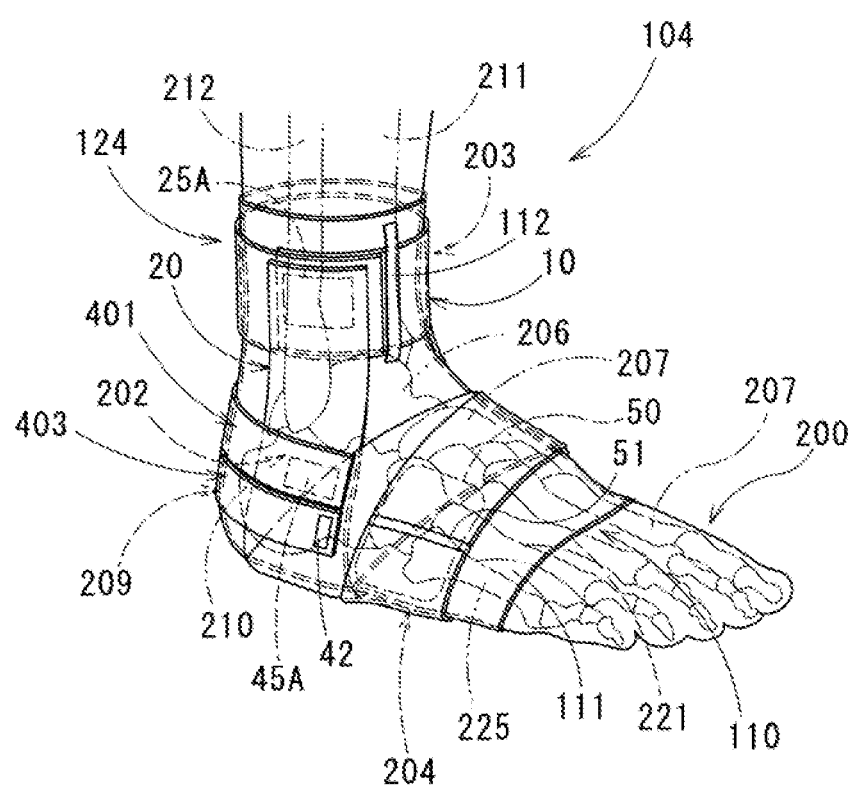
FIG. 19 It is a view showing a right foot and the heel ankle supporter according to the fifth embodiment seen from diagonally front of a fifth toe side, and showing an example of an attachment pattern of the heel ankle supporter to the foot.

A heel ankle supporter of a fourth embodiment is different from the heel ankle supporters of the first embodiment and the like in a point in which two posterior heel hold belts 401 and 402 are provided in a belt-type supporter 123 as shown in FIGS. 16 and 17.

In a heel ankle supporter 103 of the fourth embodiment, a first posterior heel hold belt 401 disposed at a position vicinity to the sole 204 below the medial malleolus 201 and the lateral malleolus 202 and a second posterior heel hold belt 402 disposed at a position vicinity to the medial malleolus 201 and the lateral malleolus 202 above the first posterior heel hold belt 401 form the posterior heel hold belts 401 and 402. The first posterior heel hold belt 401 and the second posterior heel hold belt 402 are arranged in parallel with each other, and both are fixed to the inner cover part 21 of the plantar heel hold belt 20.

In the heel ankle supporter 103 of the fourth embodiment, since the posterior heel hold belts 401 and 402 are formed from two belts which are parallel to each other, it is possible to adjust holding forces of the first posterior heel hold belt 401 and the second posterior heel hold belt 402, and to hold the foot with a suitable state in accordance with symptoms of sprain and the like.

Fifth Embodiment

A heel ankle supporter 104 of a fifth embodiment has a structure of a posterior heel hold belt being formed from two belts as in the heel ankle supporter 103 of the fourth embodiment; however, a position fixed to the plantar heel hold belt 20 is different. The first posterior heel hold belt 401 is fixed at one end thereof to the inner cover part 21 of the plantar heel hold belt 20: the second posterior heel hold belt 403 is fixed at one end thereof to the affected-part pressing belt 30 on the outer cover part 23 of the plantar heel hold belt 20.

When the heel ankle supporter 104 of the fifth embodiment is worn on the foot 200, the first posterior heel hold belt 401 and the second posterior heel hold belt 402 are arranged in positions in right and left reversed. The first posterior heel hold belt 401 is fixed at an end thereof to the plantar heel hold belt 20 on the medial malleolus 201 side and fixed by the hook surface part 45A on the inner surface at an end of the lateral malleolus 202 side: the second posterior heel hold belt 403 is fixed at an end thereof to the affected-part pressing part 30 on the plantar heel hold belt 20 on the lateral malleolus 202 side and fixed by the hook surface part 45A on the inner surface of an end of the medial malleolus 201 side.

In the heel ankle supporter 104 of the fifth embodiment, it is possible for the two posterior heel hold belts 401 and 403 to press the heel 209 from the inside to the outside and from the outside to the inside, in both directions; so that it is possible to hold the foot 200 in more suitable state in accordance with the symptoms of sprain and the like by adjusting the holding forces respectively.

Any of the heel ankle supporters 100, 101, 102, 103, and 104 explained above can reliably press important muscles, ligaments, tendons, and bones of the foot 200, and support the most important joints of the foot 200 for supporting a body, so that it is possible to reduce pain. Moreover, by the pressure added on a center part of joints, the foot 200 can be corrected into a natural and proper form. When the correction is finished, the natural axis of human's foot is adjusted; by the axis is adjusted, the following effects can be taken.

By stabilizing the axis of the foot 200, the axis of a lower body is supported, and it is possible to reduce uneasiness and pain of not only the ankle 203 but also a shin, a calf, a knee, a back of the knee, a thigh, a hip, a hip joint, and a lower back. By supporting the axis of the lower body, a trunk and a backbone are stabilized, so that it is possible to mend modern diseases such as a hunchback, a shoulder stiffness and a straight neck (a text neck) in an upper body. Moreover, it is possible to stabilize the ankle 203 to the vicinity of the tips of the toes, the talus, the calcaneus bone, the Chopart joint, the Lisfranc joint, a tibiofibular syndesmosis joint and the like can be supported.

Furthermore, by stabilizing the axis of the lower body, it is possible to prevent gonarthrosis and coxarthrosis (osteoarthritis of hip) of an aged person, bow legs and X-legs of a youngster, and deviation of the pelvis: and it is possible to mend pains of intervertebral disc displacement and spinal canal stenosis and prevent development thereof. The single supporter (among the heel ankle supporters 100, 101, 102, 103 or 104) has the effects obtained by a knee supporter and a lower-back corset and the like.

Moreover, by continuing to wear the heel ankle supporters 100, 101, 102, 103 or 104, it is possible to receive benefit of prevention, improvement and the like of symptoms below from correction of positions of the joints in the ankle 103.
1. Hallux valgus
2. Digitus minimus varus (bunionette)
3. sesamoid trouble of the first toe of the foot
4. Flatfeet, pain around the navicular bone of the foot, pain of sustentaculum tali
5. General pain of the heel (including sprain fracture, Achilles tendonitis, and rapture of Achilles' tendon), epiphysitis (osteochondritis), deformation of the heel bone, a thorn-like deformation (bone spur or osteophyte), Sever disease, posterior impingement syndrome and triangular bone disorder
6. General pain of the sole (plantar fasciitis and the like), pain around the fifth metatarsal bone (the fifth toe side of the foot), a plantar cramp, a reduction of a bending force of a toe (a reduction of a force kicking a ground), "GETA fracture" (Jones fracture or dancer's fracture)
7. A callus or a cone on the sole, a clavus, ingrown toenails, peripheral nerve disorder and angiopathy from the ankle
8. Morton disease
9. Hammer toe
10. Lisfranc joint syndrome, pain of the instep of the foot, a ganglion at the ankle
11. Talus unstable syndrome, pain of the tibiofibular syndesmosis joint
12. Chopart joint syndrome
13. Ligament affection around an ankle (anterior talofibular, medial talofibular (calcaneofibular), posterior talofibular, deltoid ligament, bifurcate ligament and the like)
14. Tarsal sinus syndrome
15. Tibiofibular syndesmosis affection
16. Tibialis posterior muscle inflammation, tibialis posterior muscle enthesitis, first and second Kohler's disease
17. Swelling, chill of foot, varicose veins
18. Pain of shin, shin neuralgia, tibiofibular joint affection
19. Shin splints
20. General pain of calf, calf neuralgia, calf cramp
21. Patellar ligamentitis
22. Osgood disease (Osgood-Schlatter disease), Hoffa syndrome (an inflammation of infrapatellar fat pad), jumper's knee, Sinding-Larsen-Johansson disease
23. Pain in knee back, popliteus inflammation, popliteus lymphoma, Baker's cyst
24. Goose foot inflammation (anserine bursitis)
25. Iliotibial band syndrome, tensor fasciae latae myositis, and greater trochanter pain accompanied therewith
26. Collateral ligament injury of right and left knees, gonarthrosis and bow legs, X-legs
27. Pain in muscles of anterior and inner thigh, pulled muscle (quadriceps muscle myositis, gracilis muscle myositis, adductor myositis and the like)
28. Pain in muscles of posterior, pulled muscle (biceps femoris muscle and the like)
29. Pain in a hip joint (coxa), pain proximal end of leg, iliopsoas muscle pain, groin pain
30. Coxarthrosis
31. Pain in gluteal muscle, and sciatica accompanied therewith, referred pain of gluteus minimus muscle, superior cluneal nerves ache
32. Sacroiliac articular lumbago and sciatica accompanied therewith
33. Muscle knots and pain around iliac crest, distortion of pelvis (difference in height, forward bent, backward tilting)
34. Pain in lower-back muscles (quadratus lumborum muscle, psoas major muscle, iliocostalis muscle) and femoral neuralgia accompanied therewith
35. Spinal canal stenosis, air intervertebral disc displacement of lower-back, a strained back
36. Myotony of abdominal muscle
37. Pain, distortion, shoulder stiffness and neck stiffness, reduction of trunk and muscle power, a wobble by single-leg standing, drag-to gait, falling-backward when squatting straight down and the like; in whole body from face to toe which are influenced by covering the above-mentioned symptoms.

It is possible to protect joints around the ankle from children to aged person by wearing the ankle-heel supporters 100, 101, 102, 103 or 104.

The present invention is not limited the above-mentioned embodiments and various modifications may be made without departing from the scope of the present invention.

For example, forming the heel ankle supporter from resin rubber or the like having water resistance and water repellent, it is possible to attach it in the water and protect human body loosened by flutter kick of swimming and the like. Considering a difference of basic states of lower leg joints in accordance with a wearer such as aged persons, young persons, and young generation, more appropriate protection and correction are possible by using material with different elasticity or modifying whole size.

Moreover, forming a scale on the outer surfaces of the belts (the ankle belt, the plantar heel hold belt, the affected-part pressing belt, the posterior heel hold belt) configuring the heel-ankle belt, it is possible to confirm that the belts are stretched to what extent for wearing.

INDUSTRIAL APPLICABILITY

The heel ankle supporter according to the present invention can be used for correcting the bones and the joints around the ankle, so that the bones, the joints and the muscles around the ankle can be stabilized.

REFERENCE SIGNS LIST 10 ankle belt
15A, 25A, 35A, 45A, 45B, 60A, 60B hook surface part
20 plantar heel hold belt
21 inner cover part
22 plantar cover part
23 outer cover part
24 fixing part
30 affected-part pressing belt
31 pressing part
32 fixing part
33 overlapped part
40, 400 posterior heel hold belt
401 first posterior heel hold belt
402, 403 second posterior heel hold belt
41 posterior cover part
42 fixing part
43 overlapped part
50 pressing pad
51 holding belt
60 instep hold belt
100, 101, 102, 103, 104 heel ankle supporter
110 sleeve supporter
111 supporter body
112 belt loops
120, 121, 123, 124 belt-type supporter
200 foot
201 medial malleolus
202 lateral malleolus
203 ankle
204 sole (of a foot)
205 Chopart joint
206 talus
207 navicular bone
208 Achilles' tendon
209 heel
210 calcaneus bone
211 tibia
212 fibula
213 Lisfranc joint
221 instep
225 fifth metatarsal bone

The invention claimed is:

1. A heel ankle supporter having elasticity attachable to a foot of a human body, comprising:
   a sleeve supporter which can cover a surface of a region including an instep, a sole, a heel and an ankle of the foot; and a belt-type-supporter-which is fixed to the sleeve supporter and attachable to the foot on the sleeve supporter, wherein
   the belt-type supporter is provided with an ankle belt, a plantar heel hold belt, an affected-part pressing belt, and a posterior heel hold belt which are respectively formed into a belt-shape:
   the ankle belt is fixable to the ankle by being wound around the ankle above a medial malleolus and a lateral malleolus of the foot:
   in the plantar heel hold belt, one end in a longitudinal direction is fixed to the ankle belt so as to extend downward from the ankle belt from the one end toward the other end; the plantar heel hold belt is provided with: an inner cover part configure to continue from the ankle belt so as to cover a vicinity of the medial malleolus; a plantar cover part configured to continue from the inner cover part so as to cover the sole at a front of a calcaneus; and an outer cover part configured to continue from the plantar cover part so as to cover a vicinity of the lateral malleolus:
   the other end of the plantar heel hold belt is fixed to an outer surface of the ankle belt so that the plantar heel hold belt is fixable to the foot passing through the sole in extended state:
   the affected-part pressing belt is fixed to the plantar heel hold belt at one end in a longitudinal direction, configured to extend diagonally forward in a direction gradually separated from the plantar heel hold belt from the one end to the other end, and provided with of pressing part which is wound in a direction from an outside of the foot to an inside of the foot through the instep side so as to cover an affected part:
   the other end of the affected-part pressing belt is fixed to any ore of outer surfaces of the ankle belt, the plantar heel held belt or the affected-part pressing belt in a middle position along a longitudinal direction so as to be fixed to the foot and cover the affected part in an extended state:
   the posterior heel hold belt is fixed to the plantar heel hold belt below the medial malleolus and the lateral malleolus at one end in a longitudinal direction; configured to extend backward from the plantar heel hold belt parallel to the ankle belt, provided with a posterior cover part so as to cover a posterior part of a vicinity of the calcaneus; and fixed to an outer surface of the outer cover part at the other end so as to be fixed to the heel of the foot covering the posterior part in an extended state: and
   the sleeve supporter is made of cloth which is more elastic than the belt-type supporter, and a thickness of yarn used for it is not smaller than 30 denier and not more than 70 denier, clothing pressure is not less than 10 mmHg but not more than 20 mmHg, and wherein
   the belt-type supporter is detachable to the sleeve supporter, and the sleeve supporter has belt loops in which the ankle belt is passed through and held.

2. The heel ankle supporter according to claim 1, wherein extension force of the sleeve supporter is larger than those of the belts of the belt-type supporter.

3. The heel ankle supporter according to claim 1, wherein the posterior heel hold belt is detachable to the belt-type supporter.

4. The heel ankle supporter according to claim 1, further comprising an instep hold belt configured to be detachable to a tip end of the sleeve supporter so as to stabilize a part including the instep and the sole by winding one or more rounds.

5. The heel ankle supporter according to claim 1, wherein the posterior heel hold belt is configured from two belts which are a first posterior heel hold belt and a second posterior heel hold belt:
- the first posterior heel hold belt is provided at a position near to the sole below the medial malleolus and the lateral malleolus; and
- the second posterior heel hold belt is provided at a position nearer to the medial malleolus and the lateral malleolus than that of the first posterior heel hold belt.

6. The heel ankle supporter according to claim 5, wherein
- the first posterior heel hold belt is fixed to an inner cover part of the plantar heel hold belt at one end; and
- the second posterior heel hold belt is fixed to an outer cover part of the plantar hold belt at one end.

7. The heel ankle supporter according to claim 1, wherein the sleeve supporter is formed from moisture absorbing heat generation cloth.

* * * * *